United States Patent
Bolotin et al.

[11] Patent Number: 6,162,462
[45] Date of Patent: Dec. 19, 2000

[54] LIPOSOMAL BUPIVACAINE COMPOSITIONS PREPARED USING AN AMMONIUM SULFATE GRADIENT

[75] Inventors: Elijah M. Bolotin, Buffalo Grove, Ill.; Gilbert J. Grant, White Plains, N.Y.; Yechezkel Barenholz, Jerusalem, Israel; Herman Turndorf, New York; Boris Piskoun, Brooklyn, both of N.Y.

[73] Assignees: New York University, New York, N.Y.; Yissum Research Development Co. of the Hebrew Univ. of Jerusalem, Jerusalem, Ill.

[21] Appl. No.: 09/372,360

[22] Filed: Aug. 11, 1999

Related U.S. Application Data

[60] Provisional application No. 60/096,331, Aug. 12, 1998.

[51] Int. Cl.[7] .................................................. A61K 9/127
[52] U.S. Cl. ........................... 424/450; 264/4.1; 264/4.3
[58] Field of Search ..................................... 424/450, 417, 424/1.21, 9.321, 9.51; 436/529; 935/54; 264/4.1, 4.7

[56] References Cited

U.S. PATENT DOCUMENTS

| | | | |
|---|---|---|---|
| 4,532,089 | 7/1985 | MacDonald | 264/4.3 |
| 5,188,837 | 2/1993 | Domb . | |
| 5,192,549 | 3/1993 | Barenholz | 424/450 |
| 5,316,771 | 5/1994 | Barenholz | 424/450 |

FOREIGN PATENT DOCUMENTS

WO 98/14171  4/1998  WIPO .

OTHER PUBLICATIONS

Pick Archives of Biochem a Biophys. 212 #1 p. 186–194, 1981.

Antimisiaris, S. G., et al., "Liposomes as vaccine carriers Incorporation of soluble and particulate antigens in giant vesicles" *Journal of Immunological Methods* 166:271–280 (1993).

International Search Report for Application No. PCT/US99/18411.

Masters, D.B., and Domb, A.J., "Liposphere Local Anesthetic Timed–Release for Perineural Site Application" *Pharmaceutical Research* 15 (7):1038–1045 (1998).

Mayer, L.D., et al., "Solute distributions and trapping efficiencies observed in freeze–thawed multilamellar vesicles" *Biochimica et Biophysica Acta* 817:193–196 (1985).

Mowat, J.J., et al., "Liposomal Bupivacaine Extended Duration Nerve Blockade Using Large Unilamellar Vesicles that Exhibit a Proton Gradient" *Anesthesiology* 85:635–643 (1996).

Turski, P., et al., "Magnetic Resonance Imaging of Rabbit Brain after Intracarotid Injection of Large Multivesicular Liposomes Containing Paramagnetic Metals and DTPA" *Magnetic Resonance in Medicine* 7:184–196 (1988).

*Primary Examiner*—Gollamudi S. Kishore
*Attorney, Agent, or Firm*—LeeAnn Gorthey

[57] ABSTRACT

Liposomal bupivacaine compositions are prepared using an ammonium sulfate gradient loading procedure, at a pH which prevents precipitation of the drug from the loading solution. Also described are liposome suspensions comprising 'GMV' (giant multivesicular) liposomes and methods for their preparation. The liposomal compositions are characterized by high drug-to-lipid ratios and provide long term analgesia.

8 Claims, 10 Drawing Sheets

LIPOSOMAL BUPIVACAINE COMPOSITIONS PREPARED USING AN AMMONIUM SULFATE GRADIENT

This application claims priority to U.S. provisional application serial No. 60/096,331, filed Aug. 12, 1998, which is hereby incorporated by reference in its entirety.

FIELD OF THE INVENTION

The present invention relates to liposomal bupivacaine compositions, useful for long term analgesia, which are prepared using an ammonium sulfate gradient loading procedure. The invention also provides methods of providing analgesia using such formulations. Also disclosed are liposome suspensions comprising 'GMV' (giant multivesicular) liposomes and methods for their preparation.

REFERENCES

Boogaerts, J. G. et al., Can J Anaesth 40(12):1201–1204 (1993).

Grant, G. J. et al., Reg Anesth 19(4):264–269 (1994).

Haran, G. et al., Biochem Biophys Acta 1151(2):201–215 (1993).

Kim, S. et al., U.S. Pat. No. 5,723,137 (1998).

Legros, F. et al., U.S. Pat. No. 5,244,678 (1993).

Mowat, J. J. et al., Anesthesiology 85(3):635–643 (1996).

Stewart, J. C. M., Anal. Biochem. 104, 10 (1959).

BACKGROUND OF THE INVENTION

Liposomal encapsulation of local anesthetics has been shown to increase the duration of pain relief. Critical factors in the effectiveness of liposomal bupivacaine formulations include encapsulation of the maximal amount of drug, as well as a suitable release rate after injection. The primary disadvantages of previously described liposomal bupivacaine formulations (e.g. Boogaerts, Grant, Legros) are relatively inefficient drug entrapment and low drug/lipid ratios. This can lead to an undesirable deposit of fatty lipid material at the site of injection.

Recently, active loading of bupivacaine using a pH gradient was described (Mowat). A sodium citrate solution was used to establish a transmembrane gradient, and a drug/lipid ratio of 0.26 was achieved, higher than that obtained previously via standard "passive" loading techniques (e.g. Legros). However, in Mowat, the extraliposomal pH was maintained at about 7.4, which potentially limits the amount of drug available for loading, as bupivacaine is poorly soluble at this pH.

SUMMARY OF THE INVENTION

The present invention includes, in one aspect, a method of producing prolonged analgesia 10 by administering a liposomal bupivacaine composition. The composition is prepared by incubating a bupivacaine solution with a suspension of liposomes having a greater concentration of ammonium ions inside said liposomes than outside said liposomes. Such a suspension is prepared by (a) vortexing a lipid film with an aqueous solution of ammonium sulfate and (b) removing ammonium sulfate from the extraliposomal medium. Preferably, the aqueous solution has a concentration of about 250 mM ammonium sulfate, and, in the incubating step, the bupivacaine solution has a pH effective to prevent precipitation of the bupivacaine; typically about 6 or less.

The method of administering of the local anesthetic compositions may also comprise cooling of the administration site. Preferably, the skin of the subject is cooled to a temperature of about 22° C. at the site of injection.

In a preferred embodiment, the liposomes are 'GMV' (giant multivesicular) liposomes. These are prepared by (a) vortexing a lipid film with an aqueous solution, such as a solution of ammonium sulfate, (b) homogenizing the resulting suspension to form a suspension of small unilamellar vesicles (SUV), and (c) repeatedly freeze-thawing said suspension of SUV in liquid nitrogen followed by water. Preferably, the freeze-thawing is repeated at least five times, and more preferably about ten times. The extraliposomal ammonium sulfate is then removed, e.g. by dialysis against normal saline. The GMV liposomes, and the disclosed method of preparation, provide additional aspects of the present invention. Preferably, the method of preparation includes encapsulating a therapeutic substance within the liposomes, e.g. by incubating a suspension of the liposomes with a solution of the therapeutic substance. Preferably, the substance is weakly basic, and the suspension of GMV liposomes has a greater concentration of ammonium ions inside the liposomes than outside the liposomes, as described above. Where the substance is bupivacaine, in the incubating step, the bupivacaine solution has a pH effective to prevent precipitation of the bupivacaine; typically about 6 or less.

The GMV-based liposomal bupivacaine compositions typically have a molar drug to lipid ratio, following removal of non-encapsulated bupivacaine, of at least 1.0. After further concentration of the resulting liposomal suspension by ultrafiltration or centrifugation, the a molar drug to lipid ratio is at least 0.5, preferably at least 1.0, and more preferably at least 1.5.

These and other objects and features of the invention will become more fully apparent when the following detailed description of the invention is read in conjunction with the accompanying drawings.

DETAILED DESCRIPTION OF THE INVENTION

I. Preparation of Liposomal BUP Formulations

A range of liposomal structures and compositions were prepared. The matrix lipid used for all formulations was hydrogenated soy phosphatidylcholine (HPC), obtained from Lipoid, Ludwigshafen, Germany, consisting of >98% distearoyl-sn-glycero-3-phosphatidylcholine (DSPC), and having a phase transition temperature of about 52.5° C. This lipid was used alone or in combination with 50 or 33 mole percent cholesterol (Chol).

Figure 1:
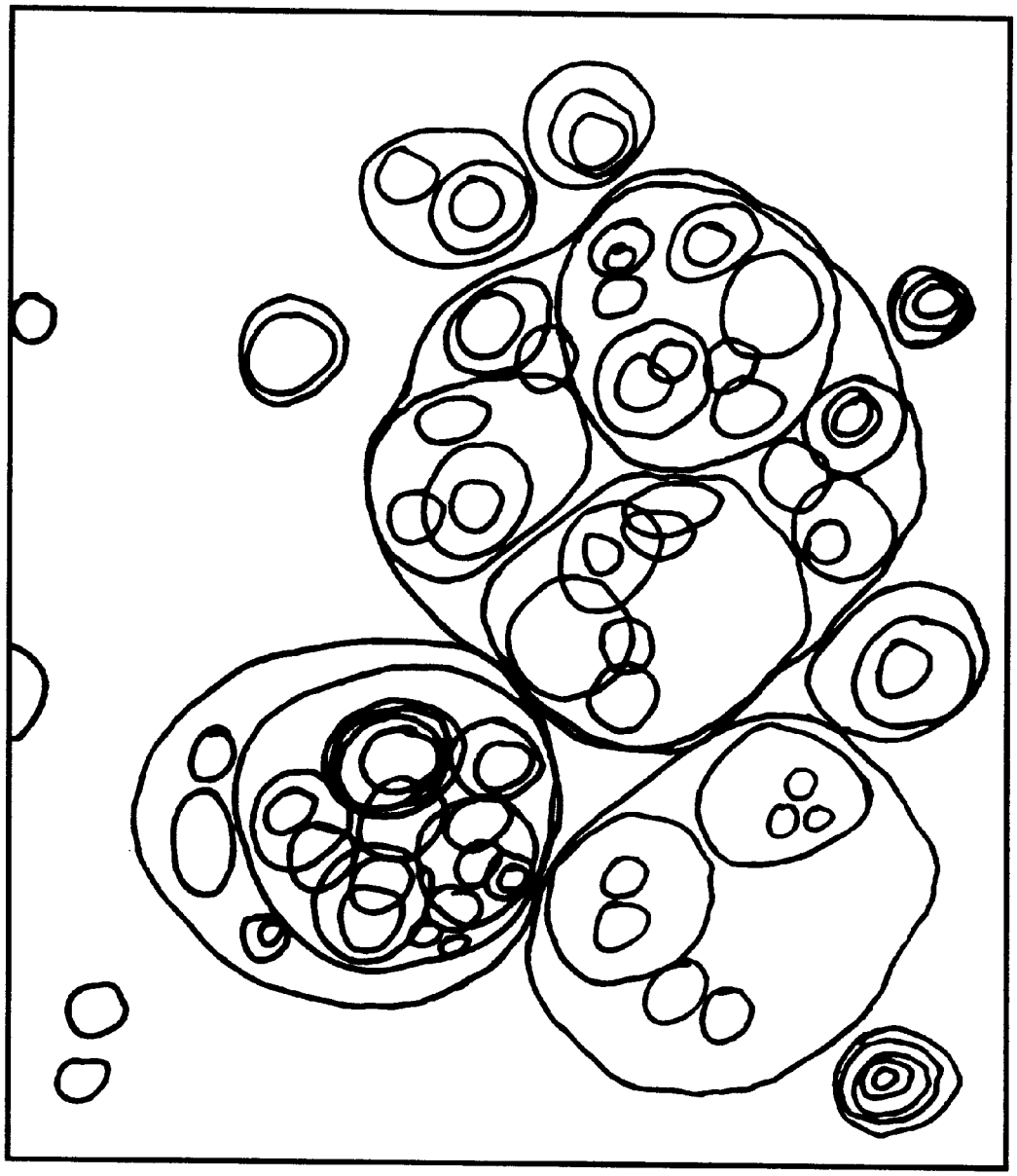
FIG. 1 is a line drawing based on a photomicrograph of the GMV liposomes described herein.

The liposomal structures prepared were small unilamellar vesicles (SUV), large unilamellar vesicles (LUV), multilamellar vesicles (MLV), and a structure denoted herein as GMV (see FIG. 1, based on a photomicrograph of these vesicles). The various structures were prepared as follows.

A thin lipid film was formed by dissolving the lipid component(s) in chloroform and removing the solvent on a rotary evaporator. MLV were formed, in accordance with known methods, by hydrating the film with a solution of ammonium sulfate (see discussion of ammonium sulfate gradient below) and vortexing at 60° C., giving a final lipid concentration of about 4%. Preferably, the concentration of the solution is about 250 mM $(NH_4)_2SO_4$. Higher concentrations (400–500 mM) were not found to be more effective.

A portion of the MLV preparation was used to form SUV, again according to known methods, by high pressure-homogenization at 10000–15000 psi (EmulsiFlex-C5, Avestin, Ottawa, ON).

GMV (FIG. 1) were prepared by freeze-thawing a portion of the SUV preparation, still suspended in the ammonium sulfate solution, in liquid nitrogen followed by immersion in 37° C. water. The freeze-thawing process was repeated ten times.

The LUV were formed by extrusion of a portion of the MLV through successively sized polycarbonate membranes (0.6, 0.4, and 0.2 μm; Nucleopore, Pleasanton, Calif.), using a Lipex Biomembranes Extruder (Vancouver, BC).

For each formulation, the extraliposomal medium was then washed of ammonium sulfate by dialysis against normal saline at 4° C., changing the dialysate three times. This is effective to create an inside-to-outside ammonium ion gradient across the liposomal membrane (Haran). The liposomal suspensions thus have a greater concentration of ammonium ions inside the liposomes than outside the liposomes; preferably, $[(NH_4)_2SO_4]_{in}/[(NH_4)_2SO_4]_{out} > 300$. The internal pH is lower than the external pH, although it must remain high enough to allow formation of ammonia from ammonium ion during the loading process. The ammonium ion concentration gradient provides the driving force for loading of amphiphilic weak bases such as bupivacaine. During incubation with a solution of the base, unprotonated compound crosses the membrane and is protonated in the lower pH interior. This raises the pH within the vesicles, leading to release of ammonia across the membrane. The process continues as long as there is an ammonium ion gradient across the liposomal membranes.

Figure 2:
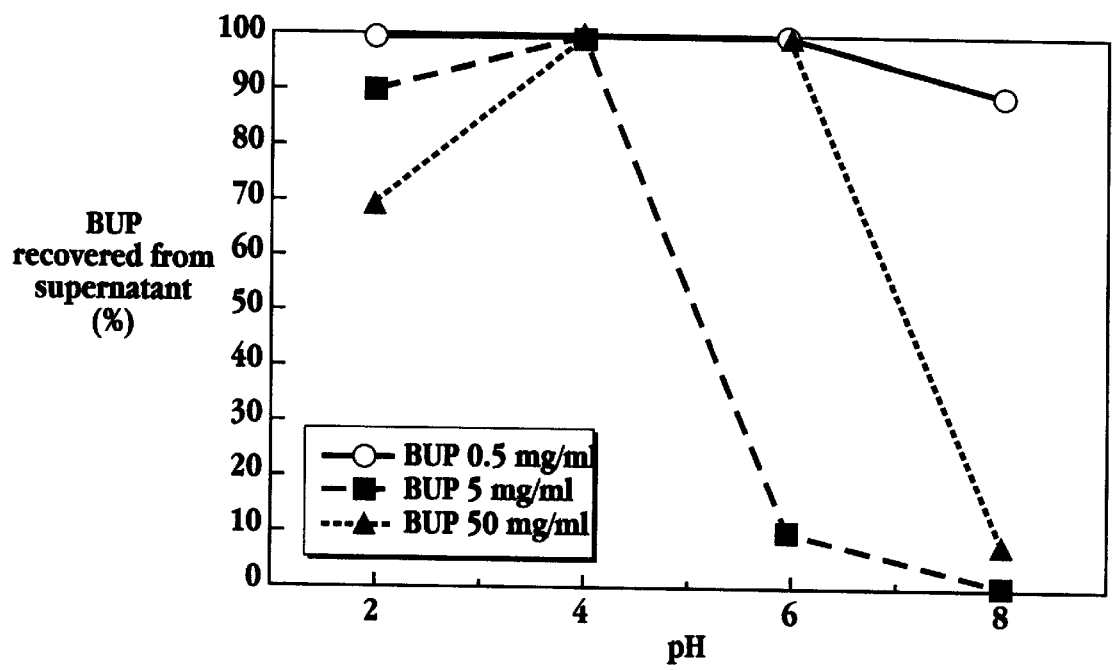
FIG. 2 shows the effect of pH on solubility of bupivacaine (BUP) at three concentrations in 250 mM ammonium sulfate.

In the present case, the liposomes were incubated with a 50 mg/ml solution of BUP HCl for 45 minutes at 60° C. During this process, the extraliposomal pH should be maintained at a pH less than about 6, e.g. about 5.5, to ensure BUP solubility and prevent precipitation. See, for example, FIG. 2, which shows the pH-dependent aqueous solubility of BUP. The data was produced by adding various levels of BUP, as indicated, to 250 mM ammonium sulfate at differing pH's. The samples were vortexed and centrifuged, and the amount of dissolved BUP in the supernatant was determined. As shown in the Figure, large amounts of BUP precipitated from the more concentrated solutions at pH's higher than about 6. In addition, Table I shows BUP partition coefficients in octanol/aqueous ammonium sulfate at various pH's. Again, aqueous solubility substantially decreases between pH 6 and 8. (Aqueous solubility is also slightly reduced at pH 2.)

TABLE I

| pH | BUP, mg/ml in octanol | BUP, mg/ml in $(NH_4)_2(SO_4)$ | BUP octanol/$(NH_4)_2(SO_4)$ partition coefficient |
|---|---|---|---|
| 2 | 2.45 | 2.30 | 1.06 |
| 4 | 1.25 | 3.32 | 0.38 |
| 6 | 1.28 | 3.62 | 0.35 |
| 8 | 4.90 | 0.32 | 15.30 |

Non-entrapped BUP was then removed from the liposomal suspensions by dialysis against normal saline. The liposomes (SUV and LUV) were concentrated by ultrafiltration (Centriprep-10 concentrator, Amicon, Beverly, Mass.) or by centrifugation at 3000G (GMV and MLV). Characteristics of these preparations are given in Table II.

Separate batches of GMV and MLV were also prepared in which centrifugation rather than dialysis was used to remove both ammonium sulfate and BUP from the extraliposomal medium. These formulations are described in Table III.

TABLE II

| Type of Liposomes | PC:Chol molar ratio | BUP after dialysis, mg/ml | PL after dialysis, mg/ml | D/PL after dialysis, mol/mol | BUP after concn., mg/ml | PL after concn., mg/ml | D/PL after concn., mol/mol (wt/wt) |
|---|---|---|---|---|---|---|---|
| SUV | 100:0 | 11.4 | 13.3 | 2.1 | 9.5 | 19.4 | 1.2 (0.49) |
| SUV | 67:33 | 3.4 | 9.4 | 0.9 | 4.9 | 61.6 | 0.2 (0.10) |
| SUV | 50:50 | 4.0 | 8.7 | 1.1 | 4.8 | 14.0 | 0.8 (0.44) |

TABLE II-continued

| Type of Liposomes | PC:Chol molar ratio | BUP after dialysis, mg/ml | PL after dialysis, mg/ml | D/PL after dialysis, mol/mol | BUP after concn., mg/ml | PL after concn., mg/ml | D/PL after concn., mol/mol (wt/wt) |
|---|---|---|---|---|---|---|---|
| LUV | 100:0 | 5.3 | 10.7 | 1.2 | 13.1 | 42.1 | 0.8 (0.33) |
| LUV | 67:33 | 4.0 | 8.3 | 1.2 | 5.1 | 24.6 | 0.5 (0.25) |
| LUV | 50:50 | 5.0 | 8.6 | 1.4 | 6.2 | 12.3 | 1.2 (0.66) |
| MLV | 100:0 | 17.1 | 15.1 | 2.8 | 32.4 | 61.3 | 1.3 (0.53) |
| MLV | 67:33 | 9.1 | 11.3 | 2.0 | 37.9 | 133.0 | 0.7 (0.35) |
| MLV | 50:50 | 5.8 | 9.2 | 1.5 | 36.7 | 145.9 | 0.6 (0.33) |
| GMV | 100:0 | 24.1 | 13.1 | 4.5 | 24.5 | 37.1 | 1.6 (0.66) |
| GMV | 67:33 | 14.8 | 11.9 | 3.0 | 34.3 | 40.6 | 2.1 (1.05) |
| GMV | 50:50 | 15.2 | 10.0 | 3.7 | 39.0 | 44.3 | 2.1 (1.16) |

TABLE III

| Type of Liposomes | Size (nm), mean | Size (nm), S.D. | HPC:Chol molar ratio | BUP after centrifugation mg/ml | PL after centrifugation mg/ml | D/PL after centrifugation (wt/wt) |
|---|---|---|---|---|---|---|
| MLV | 9770 | 1640 | 100:0 | 33.2 | 212.7 | 0.4 (0.16) |
| MLV | 5210 | 1100 | 67:33 | 27.5 | 254.5 | 0.3 (0.15) |
| MLV | 5000 | 1280 | 50:50 | 35.2 | 166.1 | 0.5 (0.28) |
| GMV | 2910 | 560 | 100:0 | 12.1 | 11.9 | 2.5 (1.00) |
| GMV | 9540 | 2030 | 67:33 | 15.7 | 35.2 | 1.1 (0.55) |
| GMV | 4320 | 1800 | 50:50 | 30.0 | 32.0 | 2.3 (1.27) |

Figure 5A:
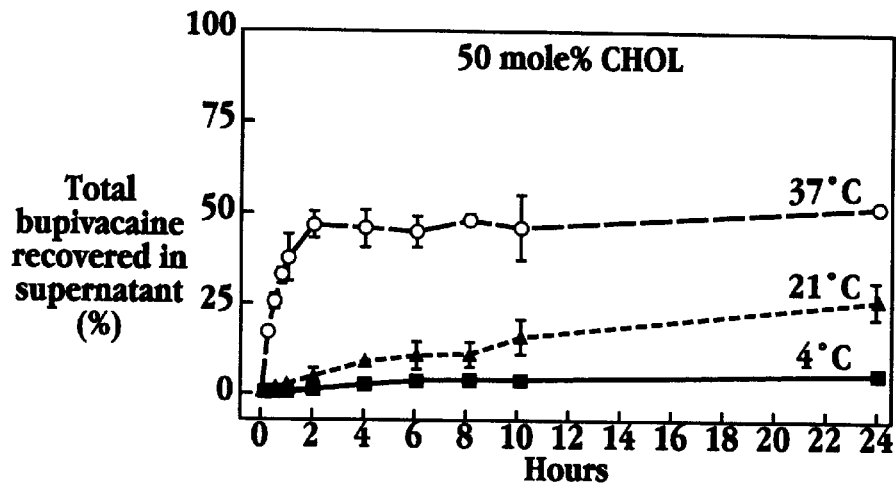
FIGS. 5A–5C show the rate of release of BUP from GMV liposomes composed of HPC/Chol (hydrogenated soy phosphatidyl choline/cholesterol) in molar ratios of 50:50 (3A), 67:33 (3B) and 75:25 (3C), at 4° C, room temperature (21° C.), and body temperature (37° C.), over 24 hours.
Figure 5B:
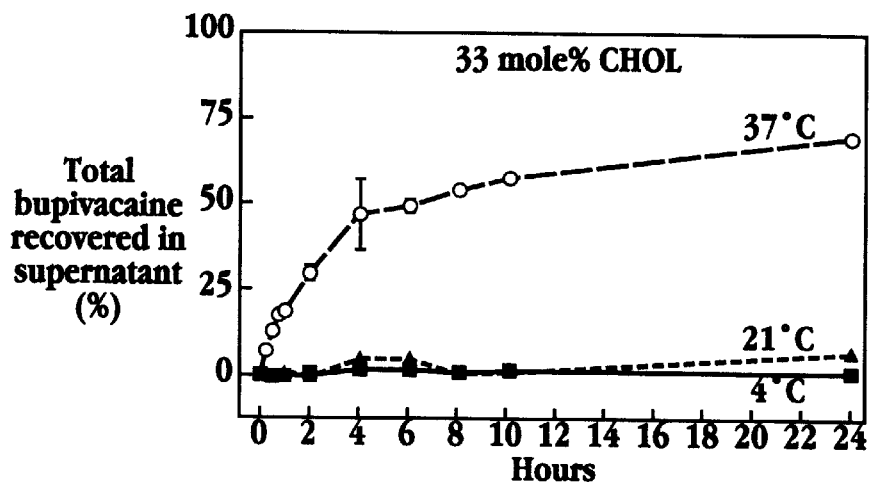
Figure 5C:
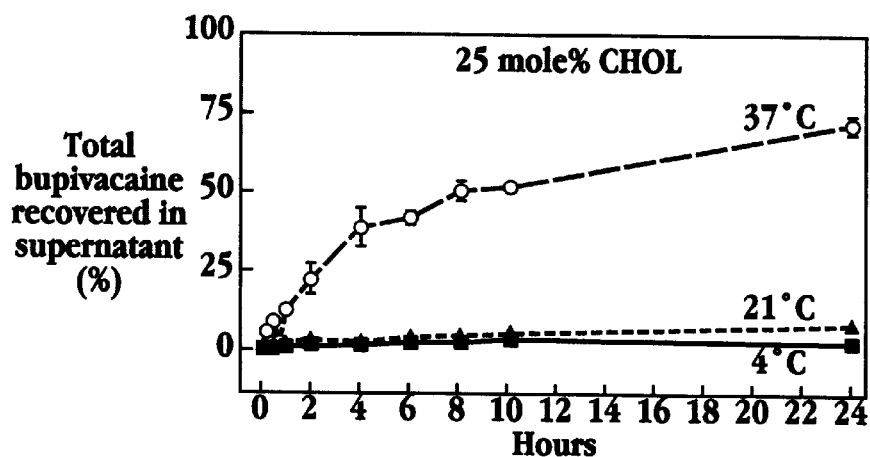

As shown below, formulations of GMV liposomes having 33–50 mole percent cholesterol and the remainder HPC were particularly effective in providing prolonged analgesia (e.g. FIG. 5), as were formulations having 40 mole % cholesterol and the remainder DMPC, DSPC, or DPPC (data not shown). However, the liposomes are not limited to these formulations, and may be formed of various combinations of vesicle-forming lipids, i.e., amphipathic lipids which have hydrophobic and polar head group moieties, and which can form bilayer vesicles in water, as exemplified by phospholipids, or which can be stably incorporated into lipid bilayers, such as sterols. The lipids typically include one or two hydrophobic acyl hydrocarbon chains or a steroid group, and may contain a chemically reactive group, such as an amine, acid, ester, aldehyde or alcohol, at the polar head group. In phospholipids, the two hydrocarbon chains are typically between about 14–22 carbon atoms in length, and have varying degrees of unsaturation. Representative examples are various phosphatidyl cholines (PC), phosphatidyl ethanolamine (PE), phosphatidic acid (PA), phosphatidyl inositol (PI), sphingomyelin (SM), negatively charged lipids such as dimyristoyl phosphatidyl glycerol (DMPG), and positively charged lipids such as 1,2-distearoyl-3-trimethylammonium propane (DSTAP).

II. Characterization

Size distribution of the liposomes was determined by photon correlation spectroscopy (N4Plus, Coulter, Miami, Fla.). The size range of the 33% Chol formulations washed by dialysis and concentrated by centrifugation (Table 2) were, in nm±S.D.: SUV, 90±150; LUV, 175±70; GMV, 2440±545; MLV, 6260±1310. Size distribution of GMV and MLV prepared using centrifugation only are given in Table 3; these sizes were seen to vary considerably with lipid composition.

Figure 3:
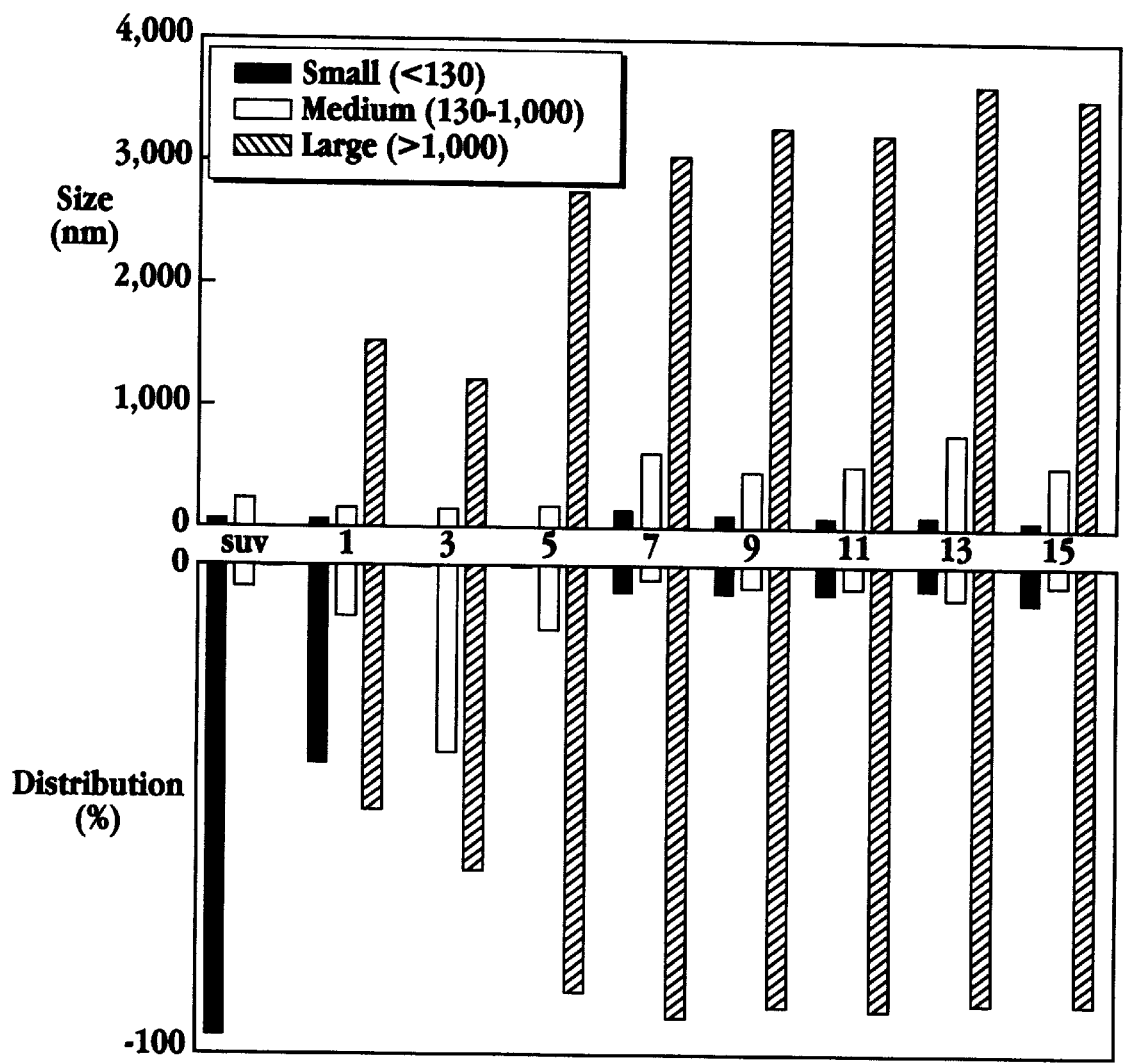
FIG. 3 shows the size and size distribution of liposomes obtained during 15 successive freeze-thaw steps in preparation of GMV.

The size and size distribution of the liposomes was also measured during preparation of GMV after each of fifteen successive freeze-thaw cycles; the results are given in FIG. 3. As shown in the Figure, the final size and distribution were approached after about five cycles.

Figure 4:
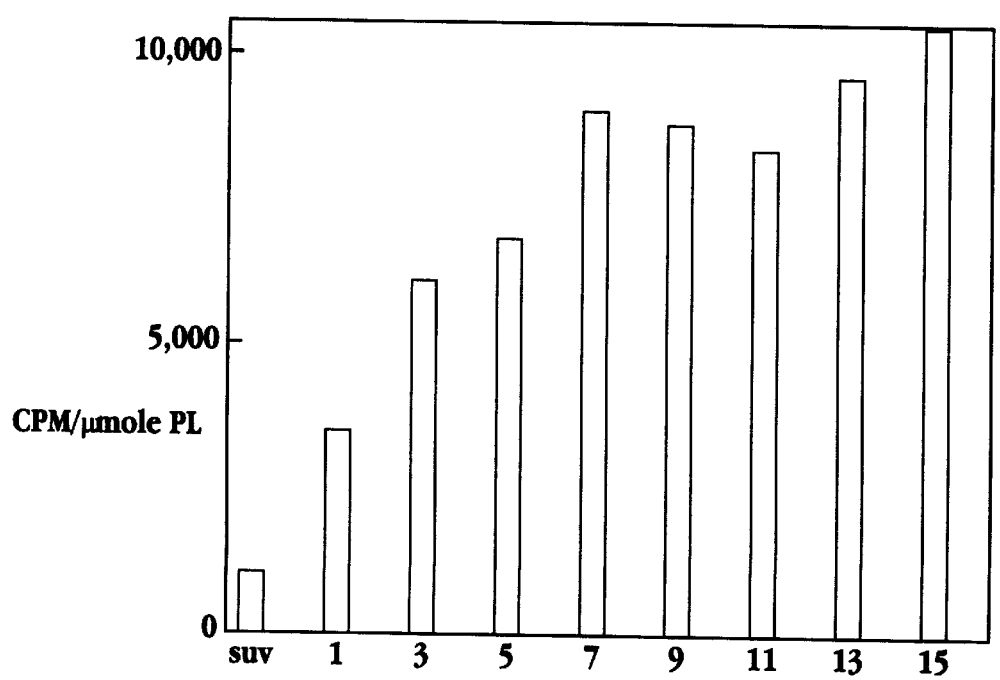
FIG. 4 shows the change in trapped volume of liposomes during 15 successive freeze-thaw steps in preparation of GMV.

The trapped volume was also determined using radiolabeled inulin. The increase in trapped volume is apparent for about the first seven cycles, as shown in FIG. 4. The ratio of trapped volume to size was found to remain constant throughout the fifteen cycles (at about 5000 CPM/$\mu$mole phospholipid), showing that increasing size did not lead to any significant leakage of contents.

A photomicrograph of the GMV liposomes is represented by the line drawing in FIG. 1. The field of view of the photomicrograph covers a range of about 1300–1400 nm (original photomicrograph taken at 45,000× and enlarged approximately 2×). Given the size range of the GMV liposomes, above, it is therefore likely that the structures shown are actually within a still larger vesicle. The liposomal structures resemble MVV (multivesicular vesicles) in that large external vesicles contain multiple, non-concentric, smaller vesicles. In comparison with previously described MVV, however, prepared by a different procedure (e.g. Kim et al.), the total lipid area/volume ratio within these structures is considerably smaller.

BUP concentration in liposomes was determined by HPLC as described in Example 1. Lipid concentration was determined using Stewart's assay (Stewart, 1959). The molar drug/lipid ratio (D/PL) for each formulation was calculated by dividing moles BUP by moles phospholipid. Tables II and III give characteristics of liposomes washed by dialysis and by centrifugation, respectively. As shown in Table II, D/PL decreased after the formulations were concentrated by ultrafiltration, but values were still significantly higher than those reported previously (i.e. 0.26 in Mowat, using a sodium citrate gradient, and about 0.1 in Legros, using standard loading techniques). Total concentration of BUP in the liposomal suspensions was as high as 3.9 wt % for the GMV liposomes, again significantly higher than previously reported. (Mowat reported an "intravesicular" BUP HCl concentration of about 100 mM. This value corresponds to about 3.25 wt %, but does not take into account the volume of the medium in which the vesicles are suspended. Accordingly, the overall concentration in the suspension would be significantly less.)

A high D/PL is especially important for administration of local anesthetics into sites such as subcutaneous tissue. In a conspicuous region, it is undesirable that a large lipid mass be retained at the site of injection for a prolonged period. The use of formulations such as described herein allows prolonged analgesia, as demonstrated below, with a minimal lipid load.

D/PL was lower overall for formulations washed by centrifugation; it is suspected that some leakage of drug occurred as a result of membrane distortion under these conditions. Greater leakage was observed in MLV and GMV liposomes having a lower cholesterol content (Table 2, columns 3 vs. 6 and 5 vs. 8). However, no consistent effect of cholesterol content on ultimate BUP concentration or D/PL ratio (columns 6 and 8) was observed.

III. In vitro Release Profiles

Release rate of BUP from the GMV liposomes (HPC/Chol at differing ratios) was evaluated at 4° C., at room temperature (21° C.), and at body temperature (37° C.). As shown in FIGS. 5A–7C, little or no drug was released into the supernatant after storage at 4° C. for 24 hrs. At room temperature, there was a gradual and steady release of the drug, with about 25% released after 24 his, in liposomes composed of 50:50 HPC/Chol, but little release in those having lower levels of cholesterol. At 37° C, a significantly greater rate of release was observed initially, particularly for the 50:50 HPC/Chol liposomes, followed by more gradual release. About 50–70% of the drug was present in the supernatant after 24 hrs.

Figure 6A:
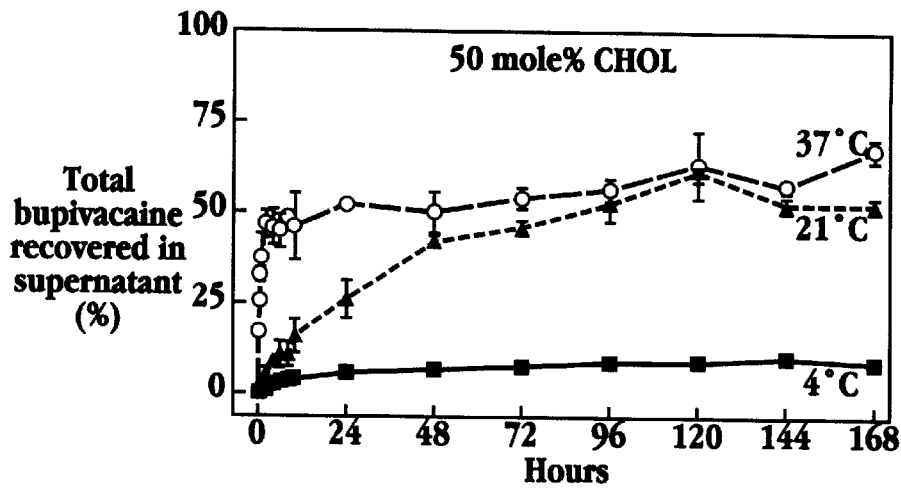
FIGS. 6A–6C show release profiles of the compositions of FIGS. 3A–3C over 7 days.
Figure 6B:
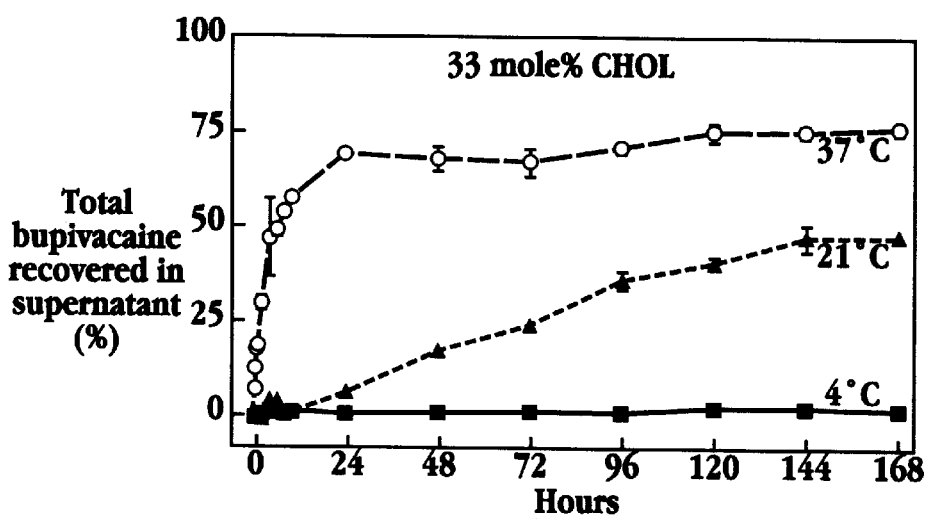
Figure 6C:
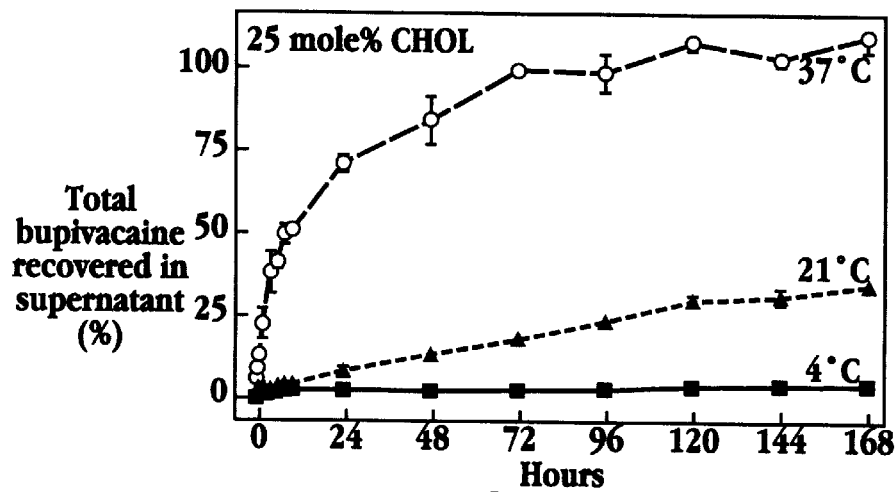

FIGS. 6A–6C show release from the same compositions over a seven-day period. Release remained negligible at 4° C., thus ensuring good storage stability, and continued at a gradual rate at 21° C. and 37° C.

These results show that the drug is released at a suitable rate at body temperature, and that the rate of release of drug can be controlled by altering the temperature. Both of these aspects add to the clinical usefulness of the compositions.

Figure 7A:
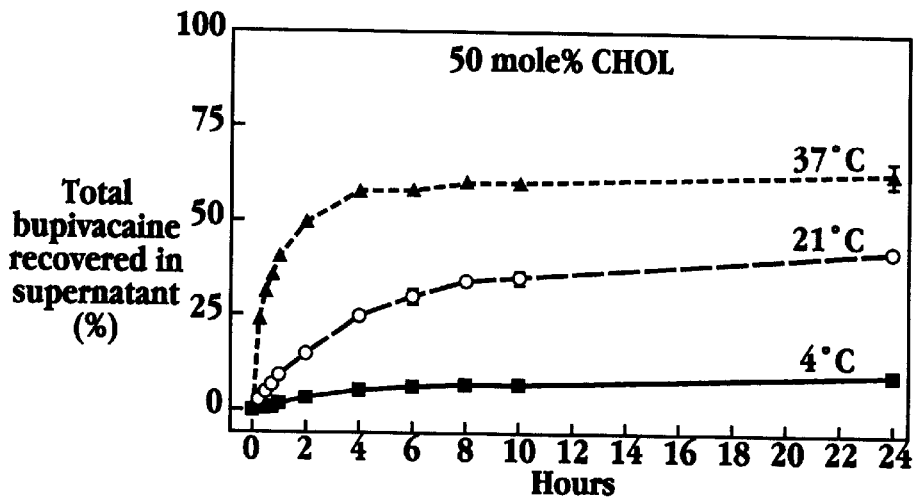
FIGS. 7A–7C show the rate of release of BUP from GMV liposomes composed of DMPC/cholesterol in molar ratios of 50:50 (3A), 67:33 (3B) and 75:25 (3C), at 4° C., 21° C., and 37° C., over 24 hours.
Figure 7B:
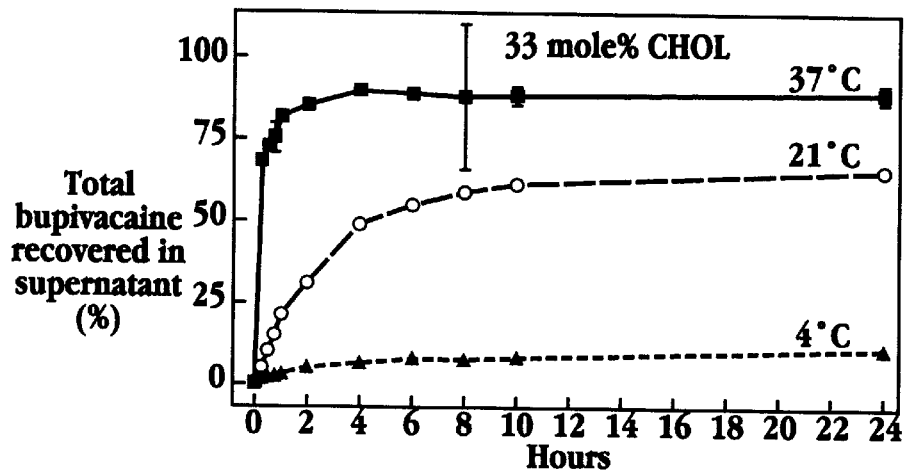
Figure 7C:
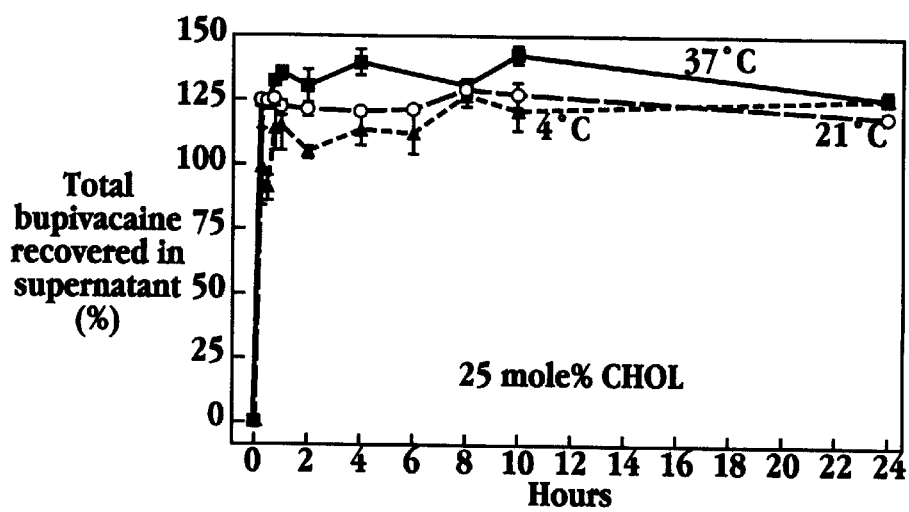

The release rate should also be amenable to manipulation by altering the constituent lipids. In general, one would expect a slower rate of release from liposomes composed of more "rigid" lipids, having higher phase transition temperatures, such as HPC, DSPC (distearoyl PC) or DPPC (dipalmitoyl PC), than a more "fluid" lipid, such as DMPC (dimyristoyl PC). This effect is demonstrated in FIGS. 7A–7C, which show bupivacaine release at the same three temperatures from GMV liposomes composed of cholesterol and 50–75% DMPC. Release was significantly faster from the 67:33 DMPC/Chol liposomes than the 50:50 HPC/Chol liposomes (FIG. 7B vs. FIG. 5B), and the 75:25 DMPC/Chol liposomes released the drug even when cold (FIG. 7C). Accordingly, both temperature and lipid composition can be manipulated to control the release rate of the drug. Manipulation of temperature in an in vivo setting is further discussed below.

IV. Analgesic Efficacy

Analgesia was assessed in male Swiss-Webster mice, as described in Example 2, using response to cutaneous electrical stimulation. Prior to administering analgesic, the control vocalization threshold (current required to produce a vocalization response) was determined. Mice which failed to respond at a cutoff current (15 mA) were excluded from the study.

For testing, 150 μl of test solution was injected subcutaneously over the abdomen, and sensory block was assessed at regular intervals, i.e., 15 min for 0.5% BUP formulations and 30 min for 1% and 2% formulations. Failure to vocalize in response to the threshold current was taken as evidence of analgesia. Testing was terminated when two successive stimuli provoked a vocalization. Duration of analgesia was taken as the time from injection to the last stimulus at which no vocalization occurred.

Figure 8:
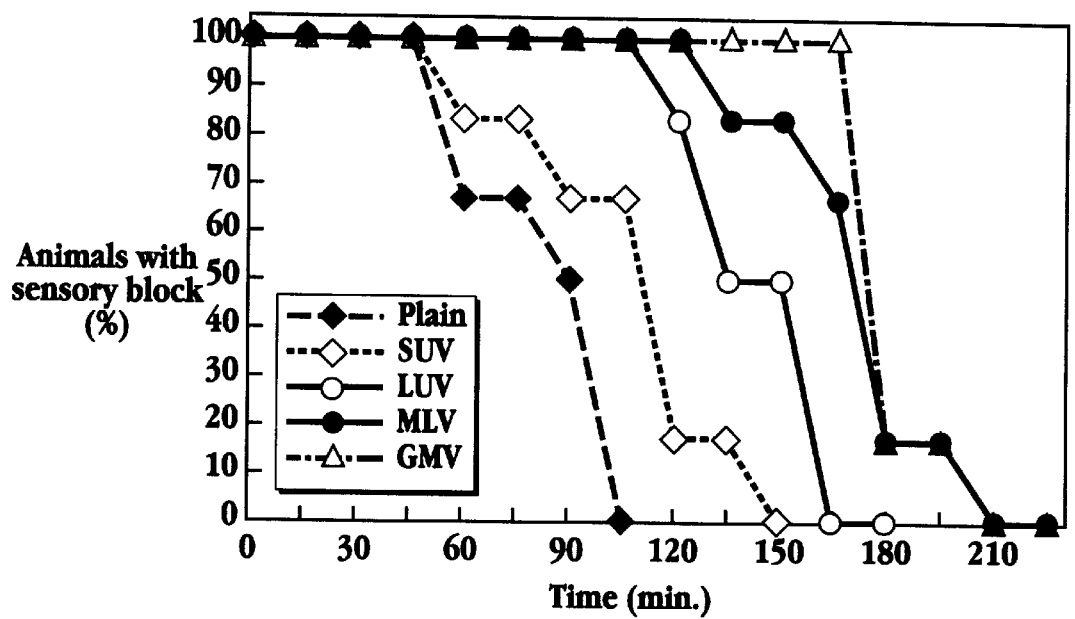
FIG. 8 shows the effect of BUP in non-liposomal and various liposomal forms, containing a 67:33 HPC/Chol lipid ratio, loaded via an ammonium sulfate gradient, on duration of sensory block after subcutaneous injection in mice.
Figure 9:
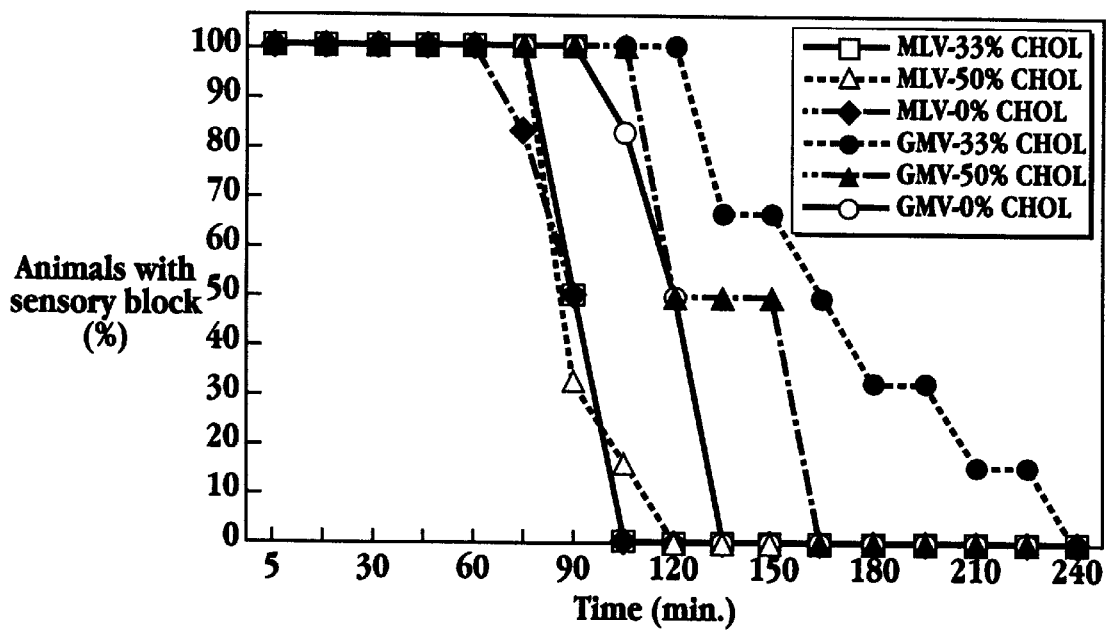
FIG. 9 shows the effect of liposome structure and Chol content on duration of analgesia.

For the data shown in FIGS. 8 and 9, all formulations were diluted to a final BUP concentration of 0.5%. (Higher concentrations of non-liposomal BUP proved toxic.) Dose-response curves, shown in FIGS. 10–12, were obtained for MLV and GMV formulations containing 1% and 2% BUP.

Results for various formulations containing 33% Chol, as characterized in Table II, are shown in FIG. 8. As shown, all formulations, except for SUV, significantly prolonged the analgesic effect relative to the control ("plain" BUP).

Figure 10:
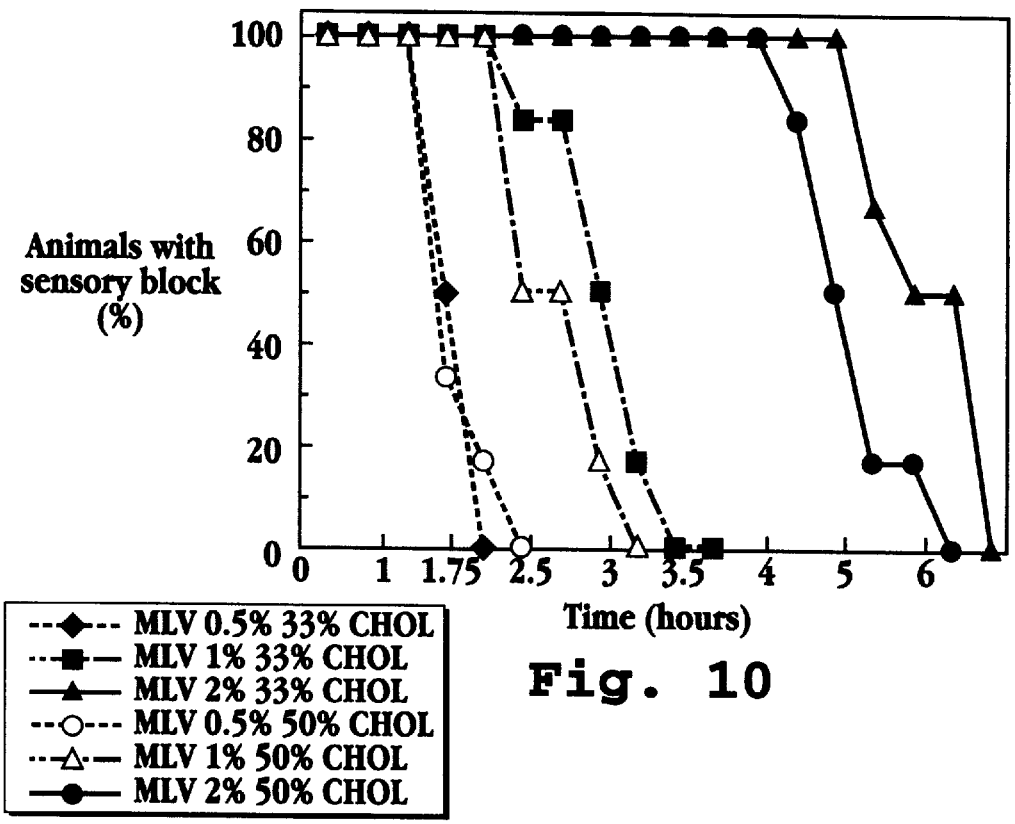
FIG. 10 shows dose-response data for 0.5%, 1% and 2% BUP in MLV containing 67:33 or 50:50 HPC/Chol.
Figure 11:
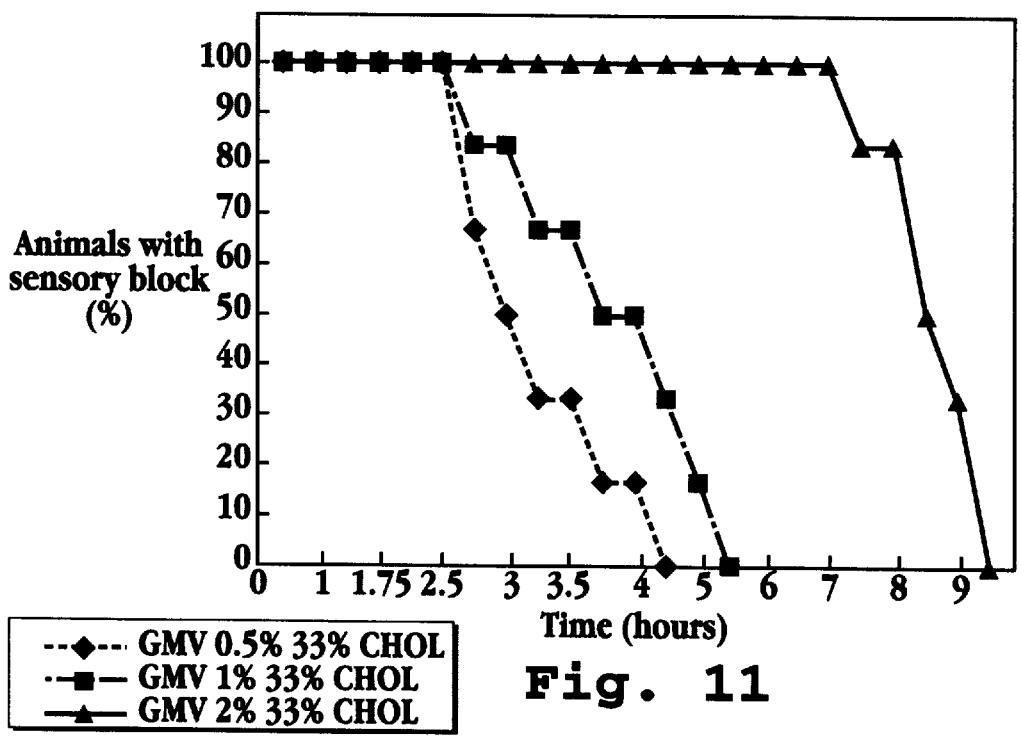
FIGS. 11–12 show dose-response data for 0.5%, 1% and 2% BUP in GMV containing, respectively, 67:33 or 50:50 HPC/Chol.
Figure 12:
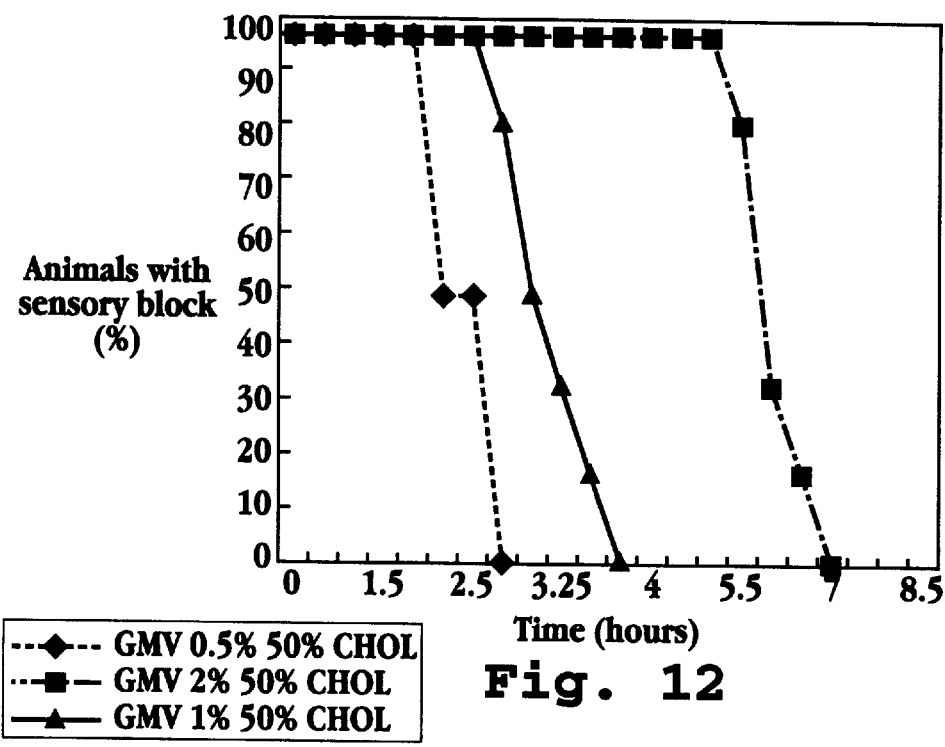

FIG. 9 shows the effect of formulations characterized in Table III. (Data shown in FIGS. 10–12 also pertains to formulations described in Table III). As shown, GMV liposomes were more effective than MLV in prolonging analgesia, particularly for the 33% Chol formulation. Dose-response curves for MLV containing 33% and 50% Chol are shown in FIG. 10. No consistent difference was observed between the different lipid compositions in this case. Similar data for the GMV liposomes, in FIGS. 11–12, show a prolonged effect for the 33% Chol composition. Comparison of FIGS. 11–12 with FIG. 10 also shows a significantly greater (prolonged) effect for the GMV liposomes as compared to the MLV.

The prolonged duration of analgesic action for the GMV compared to MLV may be related to the GMV structure, as shown in FIG. 1. The GMV liposomes provide a large encapsulated volume with fewer membranes to be traversed by the drug. Rate of release may also be regulated by altering the lipid composition, as suggested by the differing results for the 33% and 50% Chol formulations shown in FIGS. 11–12, and by the results discussed for various PC lipids above.

It was also found that local cooling of the skin at the site of administration of the liposomal formulations increased the duration of analgesia. In a control group, mice were injected with 0.15 ml nonliposomal bupivacaine at a concentration of 0.5%, the highest normally tolerated. Cooling was applied either over the injection site or over the abdomen contralateral to the injection site. (Cooling was applied by applying a small metal reservoir, about 15 mm in diameter, to the abdomen of the mouse; ice water was pumped through the reservoir to maintain the skin at a temperature of about 22° C.) There was no difference between these two groups and a group in which no cooling was applied. Analgesia regressed within two hours (see FIG. 13).

Figure 13:
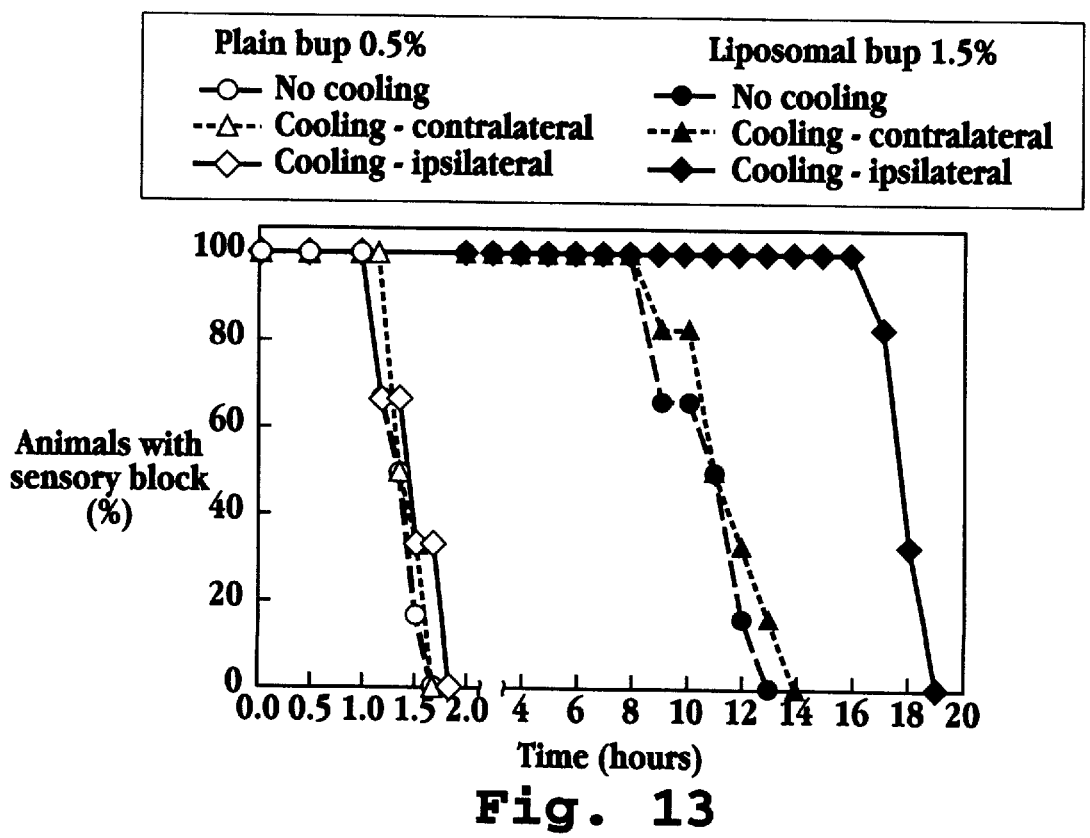
FIG. 13 shows the effect of BUP in non-liposomal and liposomal form, containing a 67:33 HPC/Chol lipid ratio, loaded via an ammonium sulfate gradient, on duration of sensory block after subcutaneous injection in mice, with and without cooling at or adjacent to the injection site.

The same test was then run using a 1.5% liposomal (GMV; 67:33 HPC/Chol) bupivacaine formulation. Analgesia was significantly prolonged in all cases, as expected, but in the group which received cooling at the site of injection, it was prolonged further, to about 19 hours vs. 13–14 hours (FIG. 13).

Figure 14A:
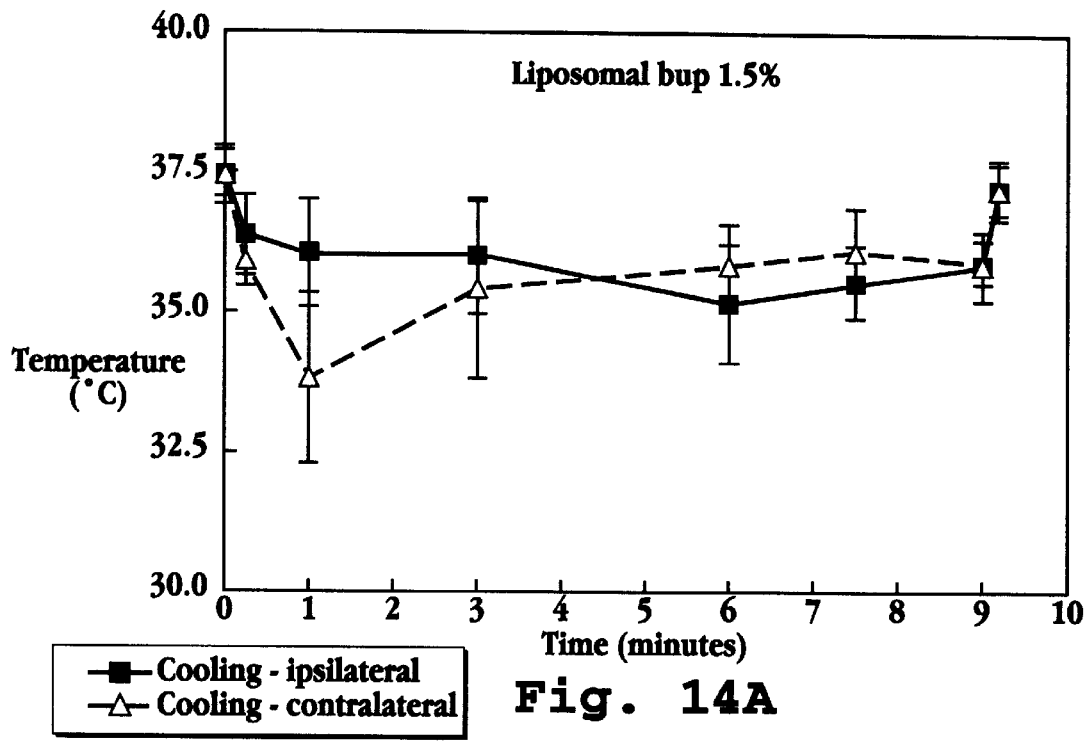
FIGS. 14A–14B show the change in body temperature over time of mice administered GMV bupivacaine (FIG. 14A; duration of cooling 9 hours) or plain bupivacaine (FIG. 14B; duration of cooling 1 hour) with cooling at (ipsalateral) or adjacent to (contralateral) the administration site.
Figure 14B:
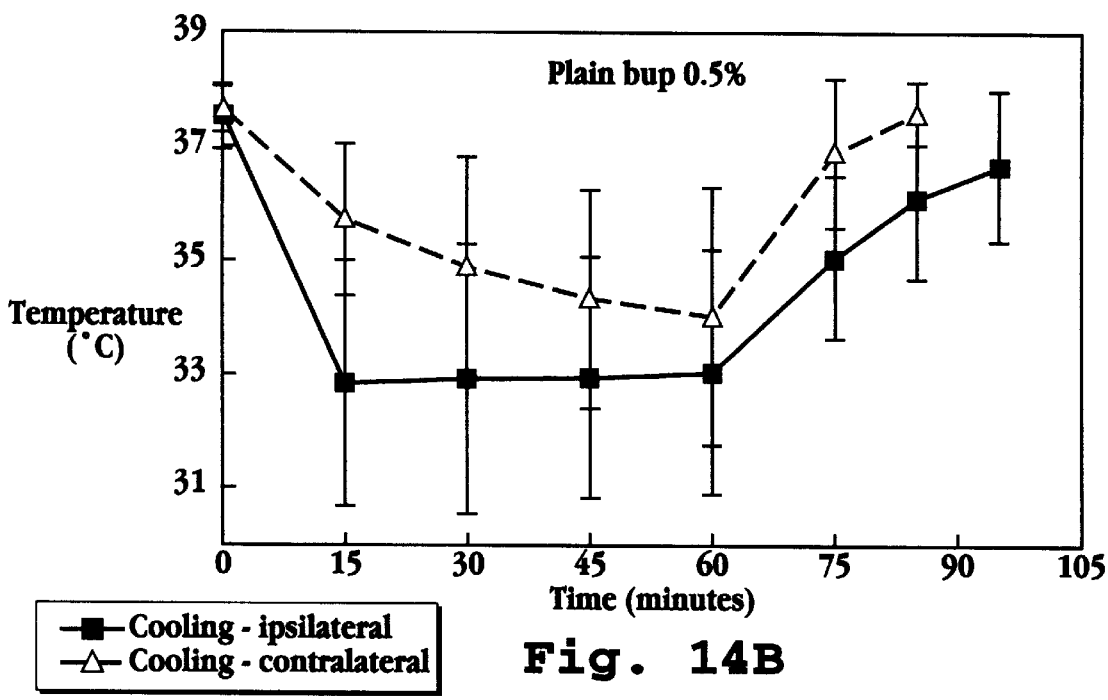

To determine the effect on overall body temperature of this treatment, the rectal temperature was measured in all animals cooled over the site of injection (ipsalateral) or over the contralateral abdomen, using both GMV-encapsulated bupivacaine and nonencapsulated (plain) bupivacaine. These results are illustrated in FIGS. 14A and 14B, respectively. For FIG. 14A, cooling was initiated at zero hours (with administration) and discontinued at nine hours; for FIG. 14B, cooling was initiated at zero hours and discontinued at one hour. There were no significant differences observed as a function of the site of cooling. The animals injected with plain bupivacaine and cooled for one hour (FIG. 14B) had a delayed return to normal body temperature (about 25–35 minutes), most likely due to a disturbance of thermoregulation induced by the high dose of bupivacaine. Animals in the GMV group (FIG. 14A) returned to baseline body temperature within about 10 minutes after cessation of cooling.

Although analgesia using bupivacaine is demonstrated herein, these methods and compositions may also be used for efficient loading and prolonged delivery of other substances, particularly weakly basic, amphiphilic drugs. Such drugs include other analgesic compounds, such as, for example, lidocaine or ropivacaine.

While the invention has been described with reference to specific methods and embodiments, it will be appreciated that various modifications may be made without departing from the invention.

EXAMPLES: Materials and Methods

Example 1. HPLC Determination of Liposomal BUP Concentration

The washed liposomes were dissolved in isopropanol (1:1000) and aliquots were injected onto an 8mm×100 mm column (Radial-Pak bNVCN, 4 μm, Waters, Milford, Mass.). A mobile phase of 25 mM acetonitrile:phosphate buffer (75:25), pH 4.0, was used, and absorption was measured at 210 nm. The retention time of BUP was approximately 4.7 minutes. Results were expressed (see Tables II and III) as mg/ml.

Example 2. Assessment of in vivo Analgesic Efficacy

The Institutional Animal Care and Use Committee approved all experiments. Male Swiss-Webster mice weighing 28±3 g were used. Animals had free access to food and water, and were maintained on a 12 hour dark-light cycle. Prior to testing, the hair overlying the abdomen was shaved. Analgesia was assessed using response to cutaneous electrical stimulation. A current generator (model S48, Grass Instruments, Quincy, Mass.) coupled to a constant current unit (model PSIU6F, Grass Instruments) was used. Current was delivered to the skin surface by gently applying two electrodes fashioned from #25 g needles. The vocalization threshold was assessed prior to testing, and testing was carried out as described above.

It is claimed:

1. A method of producing prolonged analgesia, comprising administering to a subject in need of such treatment a liposomal bupivacaine composition, wherein said composition is prepared by (i) incubating a bupivacaine solution, at a pH which prevents precipitation of the bupivacaine from the solution, with a suspension of liposomes having a greater concentration of ammonium ions inside said liposomes than outside said liposomes, and (ii) removing non-encapsulated bupivacaine, wherein said liposomes are giant multivesicular (GMV) liposomes, at least 2 microns in diameter, prepared by (a) vortexing a lipid film with an aqueous solution of ammonium sulfate, (b) homogenizing the resulting suspension to form a suspension of small unilamellar vesicles (SUV), and (c) repeatedly freeze-thawing said suspension of SUV in liquid nitrogen followed by water.

2. The composition of claim 1, wherein said pH is about 6 or less.

3. The method of claim 1, wherein said freeze-thawing is repeated at least ten times.

4. The method of claim 1, wherein said preparing of said liposomal bupivacaine composition further comprises concentrating the liposomal suspension by ultrafiltration or centrifugation.

5. The method of claim 1, wherein the molar ratio of encapsulated bupivacaine to lipid in said liposomal bupivacaine composition is at least 1.0.

6. The method of claim 5, wherein the molar ratio of encapsulated bupivacaine to lipid in said liposomal bupivacaine composition is at least 1.5.

7. The method of claim 1, further comprising cooling the site of administration of said bupivacaine composition.

8. The method of claim 7, wherein said site is cooled such that the local skin temperature is about 22° C.

* * * * *